US011020718B2

(12) United States Patent
Jones et al.

(10) Patent No.: US 11,020,718 B2
(45) Date of Patent: Jun. 1, 2021

(54) METHODS FOR FLUID MIXING SYSTEMS WITH TILTABLE SUPPORT HOUSING

(71) Applicant: LIFE TECHNOLOGIES CORPORATION, Carlsbad, CA (US)

(72) Inventors: Nephi D. Jones, Newton, UT (US); Brandon M. Knudsen, Hyrum, UT (US); Whitt F. Woods, North Ogden, UT (US)

(73) Assignee: Life Technologies Corporation, Carlsbad, CA (US)

( * ) Notice: Subject to any disclaimer, the term of this patent is extended or adjusted under 35 U.S.C. 154(b) by 397 days.

(21) Appl. No.: 16/026,771

(22) Filed: Jul. 3, 2018

(65) Prior Publication Data

US 2018/0318781 A1    Nov. 8, 2018

Related U.S. Application Data

(62) Division of application No. 14/405,126, filed as application No. PCT/US2013/027819 on Feb. 26, 2013, now Pat. No. 10,035,116.

(Continued)

(51) Int. Cl.
*B01F 15/00* (2006.01)
*C12M 1/00* (2006.01)
(Continued)

(52) U.S. Cl.
CPC .......... *B01F 15/0085* (2013.01); *B01F 7/001* (2013.01); *B01F 7/00725* (2013.01);
(Continued)

(58) Field of Classification Search
CPC .................................................. B01F 15/0085
(Continued)

(56) References Cited

U.S. PATENT DOCUMENTS

| 890,165 A | * | 6/1908 | Neal | A01J 15/06 366/238 |
| 926,760 A | * | 7/1909 | Neal et al. | A01J 15/06 366/238 |

(Continued)

FOREIGN PATENT DOCUMENTS

| EP | 1 442 785 A1 | 8/2002 |
| EP | 2 386 351 A2 | 11/2011 |

(Continued)

OTHER PUBLICATIONS

International Search Report and Written Opinion dated Oct. 21, 2013, issued in PCT Application No. PCT/US2013/027819, filed Feb. 26, 2013.

(Continued)

*Primary Examiner* — David L Sorkin
(74) *Attorney, Agent, or Firm* — Workman Nydegger

(57) ABSTRACT

A method for mixing a fluid includes: dispensing a first volume of a fluid into a flexible container, the flexible container being at least partially disposed within the chamber of a support housing; repeatedly moving the support housing and the flexible container contained therein so as to mix the first volume of fluid within the flexible container; adding further fluid into the flexible container after moving the support housing to form a second volume of fluid; and manipulating a mixing element within the flexible container so as to mix the second volume of fluid.

18 Claims, 13 Drawing Sheets

Related U.S. Application Data

(60) Provisional application No. 61/660,608, filed on Jun. 15, 2012.

(51) Int. Cl.

| | | |
|---|---|---|
| *B01F 7/00* | (2006.01) | |
| *B01F 7/16* | (2006.01) | |
| *B01F 7/22* | (2006.01) | |
| *B01F 11/00* | (2006.01) | |
| *B01F 15/02* | (2006.01) | |
| *C12M 1/06* | (2006.01) | |
| *C12M 3/06* | (2006.01) | |
| *C12M 3/00* | (2006.01) | |
| *C12M 1/02* | (2006.01) | |

(52) U.S. Cl.
CPC .......... *B01F 7/1615* (2013.01); *B01F 7/1695* (2013.01); *B01F 7/22* (2013.01); *B01F 11/0008* (2013.01); *B01F 11/0017* (2013.01); *B01F 15/0074* (2013.01); *B01F 15/00733* (2013.01); *B01F 15/00772* (2013.01); *B01F 15/0203* (2013.01); *B01F 15/0295* (2013.01); *C12M 23/14* (2013.01); *C12M 23/48* (2013.01); *C12M 23/52* (2013.01); *C12M 27/00* (2013.01); *C12M 27/02* (2013.01); *C12M 27/16* (2013.01); *C12M 29/06* (2013.01); *B01F 2015/0221* (2013.01)

(58) Field of Classification Search
USPC .................................................. 366/237–239
See application file for complete search history.

(56) References Cited

U.S. PATENT DOCUMENTS

| | | | |
|---|---|---|---|
| 1,711,114 A | 4/1929 | Hunt | |
| 2,552,057 A | 5/1951 | Paik | |
| 2,896,926 A | 7/1959 | Eric | |
| 2,982,286 A * | 5/1961 | Welch | ............... A61M 1/0245 604/245 |
| 3,117,695 A | 1/1964 | Cox, Jr. | |
| 3,328,255 A | 6/1967 | Ilg | |
| 3,583,400 A * | 6/1971 | Memhardt | .......... A61M 1/0245 604/322 |
| 4,355,906 A | 10/1982 | Ono | |
| 4,907,723 A | 3/1990 | Katz | |
| 6,908,223 B2 | 6/2005 | Bibbo et al. | |
| 7,195,394 B2 | 3/2007 | Singh | |
| 7,229,206 B2 | 6/2007 | Whitney | |
| 7,384,783 B2 | 6/2008 | Kunas et al. | |
| 7,682,067 B2 | 3/2010 | West et al. | |
| 7,879,599 B2 | 2/2011 | Goodwin et al. | |
| 7,901,934 B2 | 3/2011 | Kunas et al. | |
| 8,445,242 B2 | 5/2013 | DiCosimo et al. | |
| 8,603,805 B2 | 12/2013 | Goodwin et al. | |
| 8,641,314 B2 | 2/2014 | Thacker et al. | |
| 2002/0131654 A1 | 9/2002 | Smith et al. | |
| 2006/0240546 A1 | 10/2006 | Goodwin et al. | |
| 2006/0270036 A1 | 11/2006 | Goodwin et al. | |
| 2008/0151686 A1 * | 6/2008 | Meadows | ......... B01F 15/00883 366/274 |
| 2009/0233334 A1 | 9/2009 | Hildinger et al. | |
| 2011/0013474 A1 * | 1/2011 | Ludwig | .................... B01F 7/22 366/102 |
| 2011/0188928 A1 | 8/2011 | West et al. | |
| 2011/0310696 A1 | 12/2011 | Goodwin et al. | |
| 2013/0157355 A1 | 6/2013 | Barrett et al. | |
| 2013/0316396 A1 | 11/2013 | Fricking | |

FOREIGN PATENT DOCUMENTS

| | | |
|---|---|---|
| EP | 2 479 137 A1 | 7/2012 |
| FR | 2 630 097 A | 4/1988 |

OTHER PUBLICATIONS

International Preliminary Report on Patentability dated Dec. 24, 2014, issued in PCT Application No. PCT/US2013/032528, filed Mar. 15, 2013.
European Search Report dated Oct. 5, 2017, issued in EP Application No. 17173268.8, filed on May 29, 2017.
EP19193563.4, Extended Search Report, dated Jun. 3, 2020, 13 pages.
EP19193563.4, Partial Search Report, dated Feb. 3, 2020, 12 pages.

* cited by examiner

US 11,020,718 B2

METHODS FOR FLUID MIXING SYSTEMS WITH TILTABLE SUPPORT HOUSING

CROSS-REFERENCE TO RELATED APPLICATIONS

This application is a divisional of U.S. application Ser. No. 14/405,126, filed Dec. 2, 2014, now U.S. Pat. No. 10,035,116, which is a US nationalization of PCT Application No. PCT/US2013/027819, filed Feb. 26, 2013, which claims the benefit of U.S. Provisional application Ser. No. 61/660,608, filed on Jun. 15, 2012, and which are hereby incorporated herein by specific reference.

BACKGROUND OF THE INVENTION

1. The Field of the Invention

The present invention relates to methods of using fluid mixing systems that can function as a fermentor or bioreactor and, more specifically, to methods for fluid mixing systems having a support housing that can be selectively tilted for assembly and/or rocked or otherwise reciprocally moved for mixing fluid.

2. The Relevant Technology

The biopharmaceutical industry uses a broad range of mixing systems for a variety of processes such as in the preparation of media and buffers and in the growing, mixing and suspension of cells and microorganisms. Some conventional mixing systems, including bioreactors and fermentors, comprise a flexible bag disposed within a rigid support housing. A drive shaft projects into the flexible bag and has an impeller mounted thereon. Rotation of the drive shaft and impeller facilitates mixing and/or suspension of the fluid contained within flexible bag.

Depending on the desired processing and batch size, the support housing and the flexible bag contained therein can be relatively tall. Having a tall support housing can produce a number of complications. For example, a tall support housing can preclude passing the support housing through select doorways and thereby limit where the mixing system can be operated. Furthermore, when using tall support housings, it can be difficult to insert the flexible bag into the support housing and adjust the position thereof. This commonly requires the operator to stand on a ladder which can be precarious. In addition, where the mixing system is operating in a room with a relatively low ceiling, a tall support housing can limit the ability to vertically advance a drive shaft down into the flexible bag within the support housing, thereby further limiting where the mixing system can be used.

The impeller is typically fixed at the end of the drive shaft and is designed to remain at a substantially fixed position which is optimal for mixing a narrowly defined volume of solution in the flexible bag. To enable homogeneous mixing of larger volumes of solution, larger bags are used that have an impeller positioned at a location that is optimal for that size of bag.

In some processing procedures it can be desirable to initially mix solutions at a low volume and then progressively increase the volume of the solution. For example, this is a common procedure used with bioreactors for growing cells. The process typically entails dispensing a seed inoculum in a growth media contained within a relatively small bag or container and then transferring the solution to progressively larger bags where additional media is added as the cells grow and multiple. This process is repeated until a final desired volume is achieved. By transferring the solution to different sized bags or containers, which each have a corresponding mixer, the operator can ensure homogeneous mixing of each of the different volumes of solution. Maintaining homogeneous mixing in a bioreactor or fermentor is important to ensure proper feeding and mass transfer of gasses to the cells or microorganisms.

Although the above process of moving solutions to different sized bags to maintain proper mixing and suspension is functional, the procedure has some shortcomings. For example, the necessity of stepping to different sized bags is labor intensive, time consuming, and has high material costs in that each bag is typically discarded after use. Furthermore, transferring between different bags produces some mixing down-time which can influence cell growth. In addition, the necessity of shifting between bags increases the risk of contamination to the solution and potential damage to the cells.

Accordingly, what is needed in the art are methods and/or systems for solving all or at least some of the above problems associated with mixing systems having a tall support housing and/or transferring solutions between multiple different size bags to maintain homogeneous mixing.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

As used in the specification and appended claims, directional terms, such as "top," "bottom," "left," "right," "up," "down," "upper," "lower," "proximal," "distal" and the like are used herein solely to indicate relative directions and are not otherwise intended to limit the scope of the invention or claims.

The present invention relates to systems and methods for mixing fluids such as solutions or suspensions. The systems can be commonly used as bioreactors or fermentors for culturing cells or microorganisms. By way of example and not by limitation, the inventive systems can be used in culturing bacteria, fungi, algae, plant cells, animal cells, protozoan, nematodes, and the like. The systems can accommodate cells and microorganisms that are aerobic or anaerobic and are adherent or non-adherent. The systems can also be used in association with the formation and/or treatment of solutions and/or suspensions that are for biological purposes, such as media, buffers, or reagents. For example, the systems can be used in the formation of media where sparging is used to control the pH of the media through adjustment of the carbonate/bicarbonate levels with controlled gaseous levels of carbon dioxide. The systems can also be used for mixing powders or other components into a liquid where sparging is not required and/or where the solution/suspension is not for biological purposes.

Figure 1:
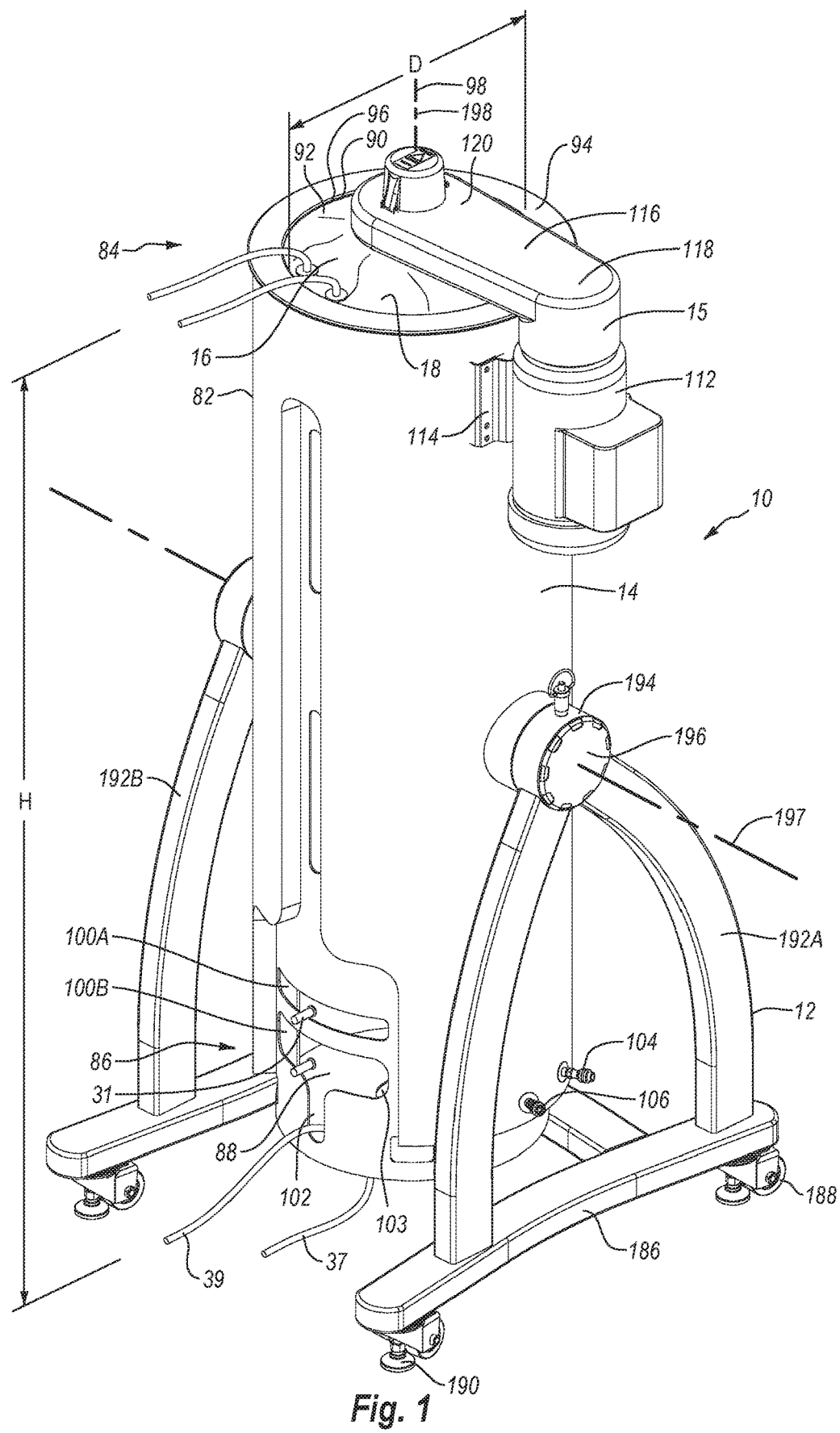
FIG. 1 is a perspective view of an inventive fluid mixing system.

Depicted in FIG. 1 is one embodiment of an inventive mixing system 10 incorporating features of the present invention. In general, mixing system 10 comprises a stand 12, a support housing 14 that is pivotably mounted to stand 12, a container assembly 16 that is supported within support housing 14, a drive motor assembly 15 mounted on support housing 14 and a drive shaft 17 (FIG. 3) that extends between drive motor assembly 15 and container assembly 16. Container assembly 16 houses the fluid that is mixed and otherwise processed. The various components of mixing system 10 will now be discussed in greater detail.

Figure 2:
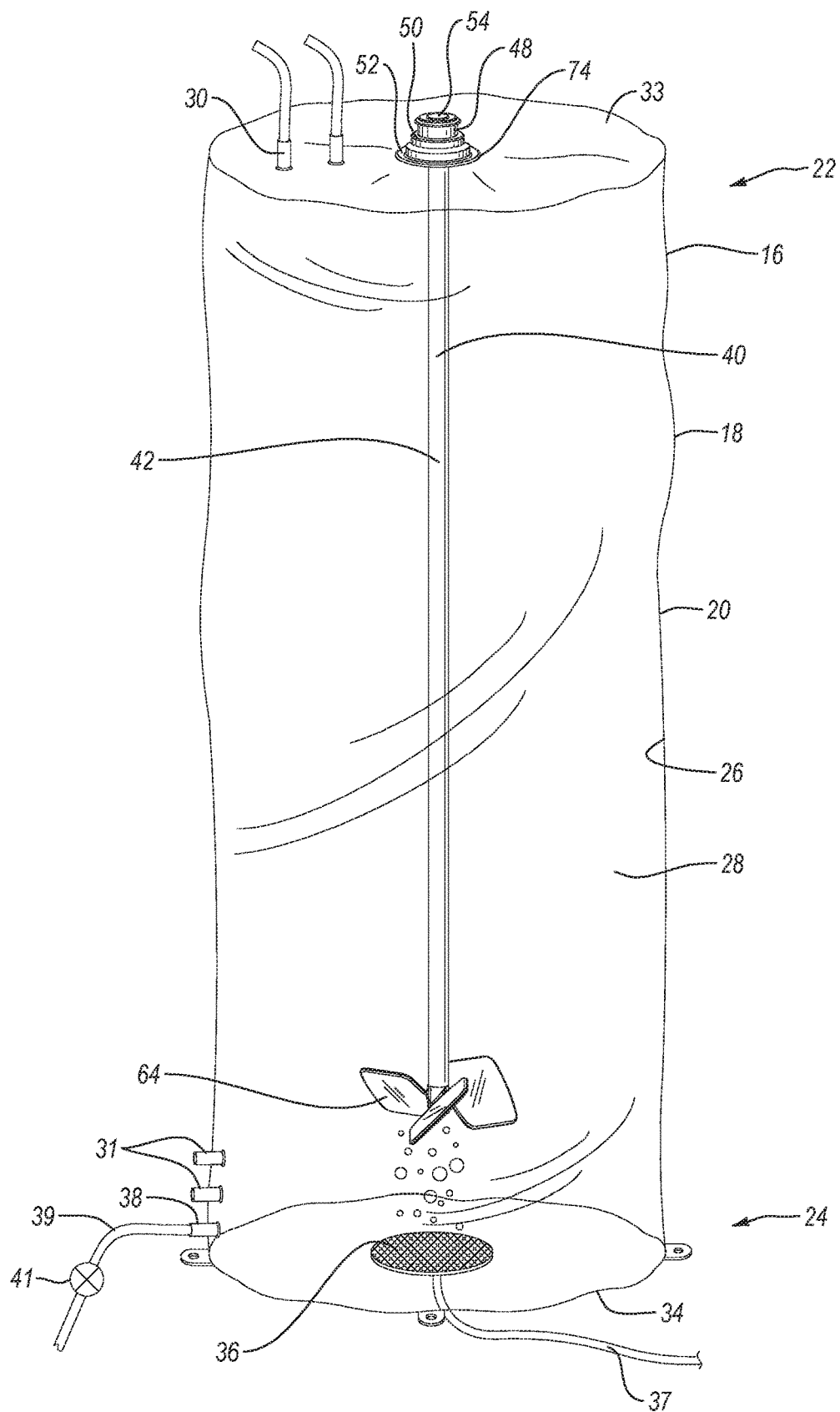
FIG. 2 is a perspective view of a container assembly of the mixing system shown in FIG. 1.

As depicted in FIG. 2, container assembly 16 comprises a container 18 having a side 20 that extends from an upper end 22 to an opposing lower end 24. Upper end 22 terminates at an upper end wall 33 while lower end 24 terminates at a lower end wall 34. Container 18 also has an interior surface 26 that bounds a compartment 28. Compartment 28 is configured to hold a fluid. In the embodiment depicted, container 18 comprises a flexible bag that is comprised of one or more sheets of a flexible, water impermeable material such as a low-density polyethylene or other polymeric film having a thickness in a range between about 0.1 mm to about 5 mm with about 0.2 mm to about 2 mm being more common. Other thicknesses can also be used. The material can be comprised of a single ply material or can comprise two or more layers which are either sealed together or separated to form a double wall container. Where the layers are sealed together, the material can comprise a laminated or extruded material. The laminated material comprises two or more separately formed layers that are subsequently secured together by an adhesive. Examples of extruded material that can be used in the present invention include the Thermo Scientific CX3-9 and Thermo Scientific CX5-14 films available from Thermo Fisher Scientific. The material can be approved for direct contact with living cells and be capable of maintaining a solution sterile. In such an embodiment, the material can also be sterilizable such as by ionizing radiation.

In one embodiment, container 18 can comprise a two-dimensional pillow style bag. In another embodiment, container 18 can be formed from a continuous tubular extrusion of polymeric material that is cut to length. The ends can be seamed closed or panels can be sealed over the open ends to form a three-dimensional bag. Three-dimensional bags not only have an annular side wall but also a two dimensional top end wall and a two dimensional bottom end wall. Three dimensional containers can comprise a plurality of discrete panels, typically three or more, and more commonly four to six. Each panel is substantially identical and comprises a portion of the side wall, top end wall, and bottom end wall of the container. Corresponding perimeter edges of each panel are seamed together. The seams are typically formed using methods known in the art such as heat energies, RF energies, sonics, or other sealing energies.

In alternative embodiments, the panels can be formed in a variety of different patterns. Further disclosure with regard to one method of manufacturing three-dimensional bags is disclosed in United States Patent Publication No. US 2002-0131654 A1, published Sep. 19, 2002 which is incorporated herein by specific reference in its entirety.

It is appreciated that container 18 can be manufactured to have virtually any desired size, shape, and configuration. For example, container 18 can be formed having a compartment sized to 10 liters, 30 liters, 100 liters, 250 liters, 500 liters, 750 liters, 1,000 liters, 1,500 liters, 3,000 liters, 5,000 liters, 10,000 liters or other desired volumes. The size of the compartment can also be in the range between any two of the above volumes. Although container 18 can be any shape, in one embodiment container 18 is specifically configured to be generally complementary to the chamber on support housing 14 in which container 18 is received so that container 18 is properly supported within the chamber.

Although in the above discussed embodiment container 18 is depicted as a flexible bag, in alternative embodiments it is appreciated that container 18 can comprise any form of collapsible container or disposable container. Container 18 can also be transparent or opaque.

Continuing with FIG. 2, formed on container 18 are a plurality of ports 30 at upper end 22 and a plurality of ports 31 at lower end 24. Each of ports 30, 31 communicate with compartment 28. Although only a few ports 30, 31 are shown, it is appreciated that container 18 can be formed with any desired number of ports 30, 31 and that ports 30, 31 can be formed at any desired location on container 18. Ports 30, 31 can be the same configuration or different configurations and can be used for a variety of different purposes. For example, ports 30 can be coupled with fluid lines for delivering media, cell cultures, and/or other components into container 18 and withdrawing fluid from container 18. Ports 30 can also be used for delivering gas to container 18, such as through a sparger, and withdrawing gas from container 18.

Ports 30, 31 can also be used for coupling probes and/or sensors to container 18. For example, when container 18 is used as a bioreactor or fermentor for growing cells or microorganisms, ports 30, 31 can be used for coupling probes such as temperatures probes, pH probes, dissolved oxygen probes, and the like. Various optical sensors and other types of sensors can also be attached to ports 30, 31. Examples of ports 30, 31 and how various probes, sensors, and lines can be coupled thereto is disclosed in United States Patent Publication No. 2006-0270036, published Nov. 30, 2006 and United States Patent Publication No. 2006-0240546, published Oct. 26, 2006, which are incorporated herein by specific reference in their entirety. Ports 30, 31 can also be used for coupling container 18 to secondary containers, to condenser systems, and to other desired fittings.

Also formed on side 20 below ports 31 so as to be adjacent to lower end wall 34 is a drain port 38 having a drain line 39 coupled thereto. As will be discussed below in greater detail, as a result of being able to tilt support housing 14 containing container 18, improved or a more complete draining can be accomplished through drain line 39 relative to traditional draining.

Mounted on lower end wall 34 is a sparger 36 having a gas line 37 coupled thereto. Sparger 36 is designed to deliver gas bubbles to the culture or other fluid within container 18 for oxygenating and/or regulating content of various gases within the culture/fluid. As needed, a second or more spargers can be mounted on lower end wall 34. The spargers can be the same or different configurations. For example, one sparger can be designed to deliver small bubbles for oxygenating while a second sparger can be designed to deliver larger bubbles for stripping $CO_2$ from the culture/fluid. In some forms of the invention, one of the spargers can be an open tube or a tube with a porous frit with relatively large pores, while the other sparger can be a tube with a porous frit with relatively small pores. The sparger can also comprise a perforated or porous membrane that is mounted on the end of a port or on the interior surface of lower end wall 34 so as to extend over a port. It is appreciated that spargers come in a variety of different configurations and that any type of spargers can be used as desired or as appropriate for the expected culture volumes, cells, fluids and other conditions. In some uses of mixing system 10, a sparger may not be required and thus sparger 36 can be eliminated.

It is appreciated that the various gas lines, fluid lines, spraging lines, drain lines and/or the like can be coupled to container 18 at the time of manufacture so that they can be sterilized concurrently with container 18. Alternatively, the lines can be connected to container 18 either prior to or after inserting container 18 into support housing 14 or prior to or after container 18 is tilted or rocked within support housing 14, as will be discussed below. The lines are typically long enough so that support housing 14 containing container 18 can be rocked or tilted during operation without interfering with the operation of the lines. In other embodiments, some lines may be disconnected from container 18 prior to tilting or rocking of support housing 14 and then reconnected after tiling or rocking of support housing 14 with container 18. The lines can be connected to container 18 using commonly known aseptic connectors.

Figure 3:
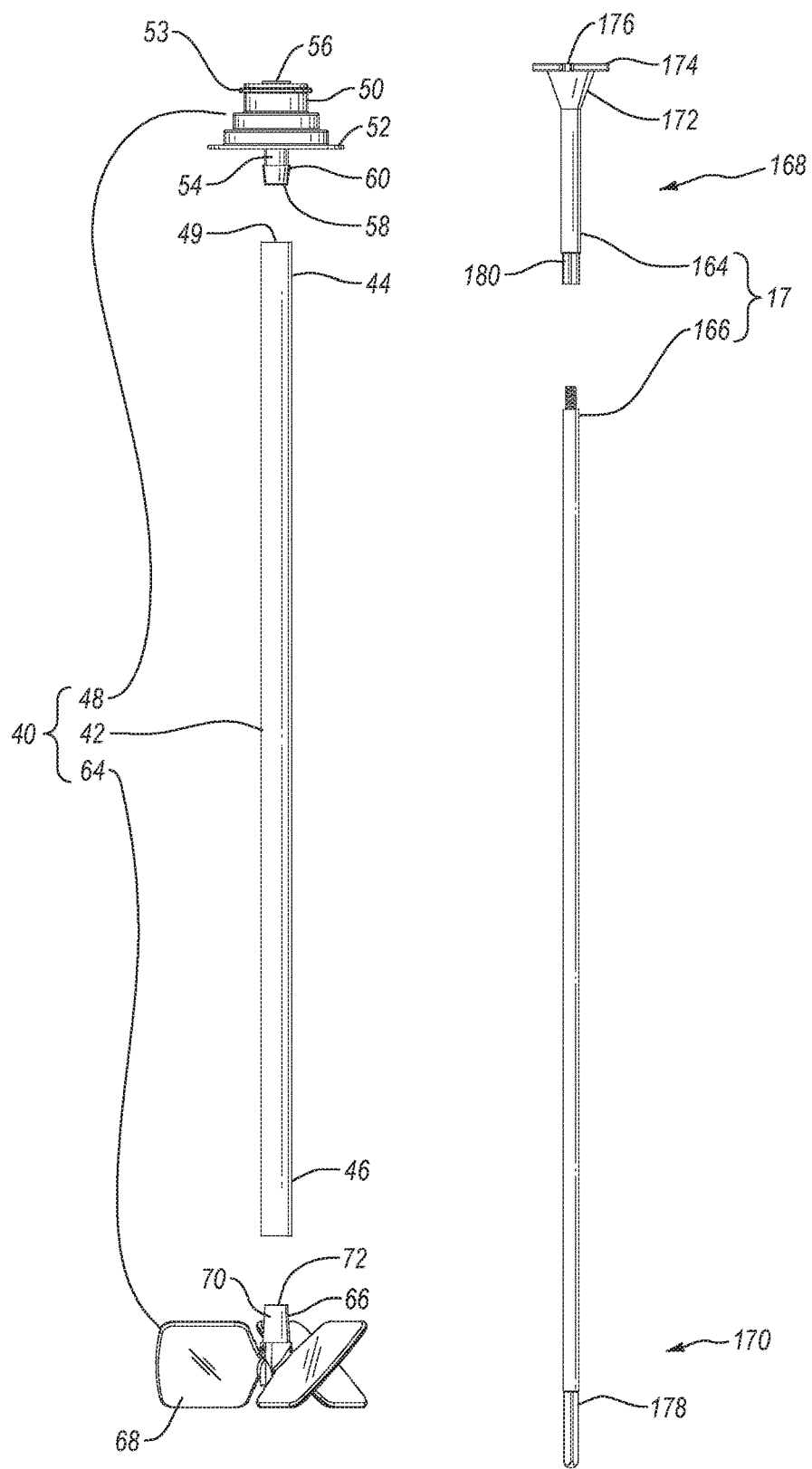
FIG. 3 is a elevated side view of an impeller assembly of the container assembly shown in FIG. 2 with a drive shaft that is removably receivable within the impeller assembly.

Container assembly 16 further comprises an impeller assembly 40. As depicted in FIG. 3, impeller assembly 40 comprises an elongated tubular connector 42 having a rotational assembly 48 mounted at one end and an impeller 64 mounted on the opposing end. More specifically, tubular connector 42 has a first end 44 and an opposing second end 46 with a passage 49 that extends therebetween. In one embodiment, tubular connector 42 comprises a flexible tube such as a polymeric tube. In other embodiments, tubular connector 42 can comprise a rigid tube or other tubular structure.

Figure 4:
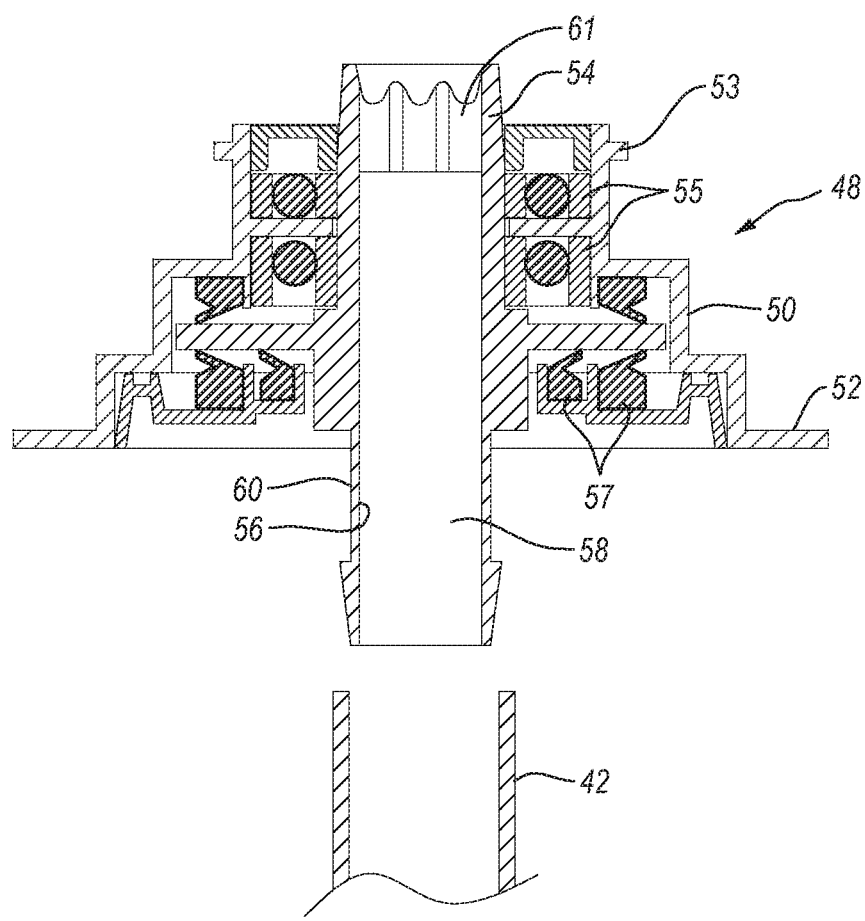
FIG. 4 is a cross sectional side view of a rotational assembly of the impeller assembly shown in FIG. 3.

Rotational assembly 48 is mounted to first end 44 of tubular connector 42. As depicted in FIG. 4, rotational assembly 48 comprises an outer casing 50 having an outwardly projecting annular sealing flange 52 and an outwardly projecting mounting flange 53. A tubular hub 54 is rotatably disposed within outer casing 50. One or more bearing assemblies 55 can be disposed between outer casing 50 and hub 54 to permit free and easy rotation of hub 54 relative to casing 50. Likewise, one or more seals 57 can be formed between outer casing 50 and hub 54 so that during use an aseptic seal can be maintained between outer casing 50 and hub 54.

Hub 54 has an interior surface 56 that bounds an opening 58 extending therethrough. As will be discussed below in greater detail, interior surface 56 includes an engaging portion 61 having a polygonal or other non-circular transverse cross section so that a driver portion 180 of drive shaft 17 (FIG. 3) passing through opening 58 can engage engaging portion 61 and facilitate rotation of hub 54 by rotation of drive shaft 17. Hub 54 can also comprise a tubular stem 60 projecting away from outer casing 50. Returning to FIG. 3, hub 54 can couple with first end 44 of tubular connector 42 by stem 60 being received within first end 44. A pull tie, clamp, crimp or other fastener can then be used to further secure stem 60 to tubular connect 42 so that a liquid tight seal is formed therebetween. Other conventional connecting techniques can also be used.

Impeller 64 comprises a central hub 66 having a plurality of blades 68 radially outwardly projecting therefrom. In the embodiment depicted, blades 68 are integrally formed as a unitary structure with hub 66. In other embodiments, blades 68 can be separately attached to hub 66. It is appreciated that a variety of different numbers and configurations of blades 68 can be mounted on hub 66. Hub 66 has a first end 70 with a blind socket 72 formed thereat. Socket 72 typically has a noncircular transverse cross section, such as polygonal, so that it can engage a driver portion 178 of drive shaft 17. Accordingly, as will be discussed below in greater detail, when driver portion 178 is received within socket 72, driver portion 178 engages with impeller 64 such that rotation of drive shaft 17 facilities rotation of impeller 64.

Impeller 64 can be attached to connector 42 by inserting first end 70 of hub 66 within connector 42 at second end 46. A pull tie, clamp, crimp, or other type of fastener can then be cinched around second end 46 of connector 42 so as to form a liquid tight sealed engagement between impeller 64 and connector 42.

Turning to FIG. 2, rotational assembly 48 is secured to container 18 so that tubular connector 42 and impeller 64 extend into or are disposed within compartment 28 of container 18. Specifically, in the depicted embodiment container 18 has an opening 74 at upper end 22. Sealing flange 52 of outer casing 50 is sealed around the perimeter edge bounding opening 74 so that hub 54 is aligned with opening 74. Tubular connector 42 having impeller 64 mounted on the end thereof projects from hub 54 into compartment 28 of container 18. In this configuration, outer casing 50 is fixed to container 18 but hub 54, and thus also tubular connector 42 and impeller 64, can freely rotate relative to outer casing 50 and container 18. As a result of rotational assembly 48 sealing opening 74, compartment 28 is sealed closed so that it can be used in processing sterile fluids.

As depicted in FIG. 3, impeller assembly 40 is used in conjunction with drive shaft 17. In general drive shaft 17 comprises a head section 164 and a shaft section 166 that can be coupled together by threaded connection or other techniques. Alternatively, drive shaft 17 can be formed as a single piece member or from a plurality of attachable sections. Drive shaft 17 has a first end 168 and an opposing second end 170. Formed at first end 168 is a frustoconical engaging portion 172 that terminates at a circular plate 174. Notches 176 are formed on the perimeter edge of circular plate 174 and are used for engaging drive shaft 17 with drive motor assembly 15 as will be discussed below.

Formed at second end 170 of drive shaft 17 is driver portion 178. Driver portion 178 has a non-circular transverse cross section so that it can facilitate locking engagement within hub 66 of impeller 64 as discussed above. In the embodiment depicted, driver portion 178 has a polygonal transverse cross section. However, other non-circular shapes can also be used. Driver portion 180 is also formed along drive shaft 17 toward first end 168. Driver portion 180 also has a non-circular transverse cross section and is positioned so that it can facilitate locking engagement within engaging portion 61 (FIG. 4) of rotational assembly 48 as discussed above.

During use, as will be discussed below in further detail, drive shaft 17 is advanced down through hub 54 of rotational assembly 48, through tubular connector 42 and into hub 66 of impeller 64. As a result of the interlocking engagement of driver portions 178 and 180 with hubs 66 and 54, respectively, rotation of drive shaft 17 by drive motor assembly 15 (FIG. 1) facilitates rotation of hub 54, tubular connector 42 and impeller 64 relative to outer casing 50 of rotational assembly 48 and container 18. As a result of the rotation of impeller 64, fluid within container 18 is mixed.

It is appreciated that impeller assembly 40, drive shaft 17 and the discrete components thereof can have a variety of different configuration and can be made of a variety of different materials. Alternative embodiments of and further disclosure with respect to impeller assembly 40, drive shaft 17, and the components thereof are disclosed in U.S. Pat. No. 7,384,783, issued Jun. 10, 2008 and US Patent Publication No. 2011/0188928, published Aug. 4, 2011 which are incorporated herein in their entirety by specific reference.

Returning to FIG. 1, support housing 14 has a substantially cylindrical sidewall 82 that extends between an upper end 84 and an opposing lower end 86. Lower end 86 has a floor 88 mounted thereto. As a result, support housing 14 has an interior surface 90 that bounds a chamber 92. An annular lip 94 is formed at upper end 84 and bounds an access opening 96 to chamber 92. As discussed above, chamber 92 is configured to receive container assembly 16 so that container 18 is supported therein.

Although support housing 14 is shown as having a substantially cylindrical configuration, in alternative embodiments support housing 14 can have any desired shape capable of at least partially bounding a compartment. For example, sidewall 82 need not be cylindrical but can have a variety of other transverse, cross sectional configurations such as polygonal, elliptical, or irregular. Furthermore, it is appreciated that support housing 14 can be scaled to any desired size. For example, it is envisioned that support housing 14 can be sized so that chamber 92 can hold a volume of less than 50 liters, more than 10,000 liters or any of the other volumes or range of volumes as discussed above with regard to container 18. Support housing 14 is typically made of metal, such as stainless steel, but can also be made of other materials capable of withstanding the applied loads of the present invention.

While support housing 14 can have any desired dimensions, in one embodiment support housing 14 can be elongated with a relatively small diameter. Specifically, when mixing system 10 is used as a fermentor, it is desirable to have a high mixing rate of the culture within container 18 to maintain consistent oxygenation and nutrient content throughout the culture. The mixing efficiency is increased by support housing 14 and corresponding container 18 having a relatively small diameter so that the culture is maintained relatively close to impeller 64. Because the diameter is relatively small, to enable batch processing at traditional volumes, the height of support housing 14 and corresponding container 18 can be long relative to the diameter. Having a relatively tall support housing 14 and corresponding container 18 also increases the resident time of the sparged gas bubbles within container 18, thereby increasing the mass transfer of the gas into the fluid. Again, this has increased importance where mixing system 10 is used as a fermentor.

By way of example and not by limitation, chamber 92 of support housing 14 can have a central longitudinal axis 98 that extends through floor 88 and access opening 96. Chamber 92 can have a maximum transverse diameter D that is normal to axis 98 and a height H that that extends along longitudinal axis 98 between floor 88 and access opening 96. Chamber 92 can be made with diameter D being between about 15 cm to about 225 cm and a corresponding height H being between about 35 cm to about 500 cm. The ratio of height H to diameter D to can be in a range between about 1 to about 10 with about 1.2 to about 4 and about 1.6 to about 3.3 being more common. In some embodiments, the ratio can be greater than 1.5, 2, 2.5, 3, 4, or 5. Again, other dimensions and ratios can also be used depending on the intended use for mixing system 10. It is appreciated that the diameters and heights as discussed above with regard to support housing 14 are also applicable to the diameter and height of container 18 when positioned within support housing 14. In addition, by making support housings 14 elongated with a relatively small diameter, mixing system 10 can be passed through normal or narrow doorways through which traditionally sized mixing system would not fit. As such, mixing systems 10 can be used in a broader range of locations.

Extending through sidewall 82 of support housing 14 at lower end 86 are slots 100A and 100B that extend horizontally and are vertically spaced apart. Slots 100A and B are designed to receive corresponding rows of ports 31. As previously mentioned, any number of ports 31 can be formed on container 18. In turn, as also previously discussed, sensors, probes, fluid lines, and the like can be coupled with ports 31 so as to communicate with compartment 28 of container 18. A vertical slot 102 also passes through sidewall 82 and extends down from slot 100B. In this configuration, slot 102 terminates close to floor 88. Drain port 38 and/or drain line 39 extend out through slot 102. In other embodiments, drain line 39 can extend out through other openings formed on sidewall 82 or on floor 88. Drain line 39 is typically coupled to container 18 through drain port 38 that is spaced apart from floor 88 but is located within 20 cm from floor 88 of support housing 14 and more commonly within 15 cm or 7 cm from floor 88. Other locations can also be used. An opening 103 extends through floor 88 through which gas line 37 passes out.

In one embodiment of the present invention means are provided for regulating the temperature of the fluid that is contained within container 18 when container 18 is disposed within support housing 14. By way of example and not by limitation, sidewall 82 can be jacketed so as to bound one or more fluid channels that encircle sidewall 82 and that communicate with an inlet port 104 and an outlet port 106. A fluid, such as water or propylene glycol, can be pumped into the fluid channel through inlet port 104. The fluid then flows in a pattern around sidewall 82 and then exits out through outlet port 106.

By heating or otherwise controlling the temperature of the fluid that is passed into the fluid channel, the temperature of support housing 14 can be regulated which in turn regulates the temperature of the fluid within container 18 when container 18 is disposed within support housing 14. In an alternative embodiment, electrical heating elements can be mounted on or within support housing 14. The heat from the heating elements is transferred either directly or indirectly to container 18. Alternatively, other conventional means can also be used such as by applying gas burners to support housing 14 or pumping the fluid out of container 18, heating the fluid and then pumping the fluid back into container 18. When using container 18 as part of a bioreactor or fermentor, the means for heating can be used to heat the culture within container 18 to a temperature in a range between about 30° C. to about 40° C. Other temperatures can also be used.

Figure 6:
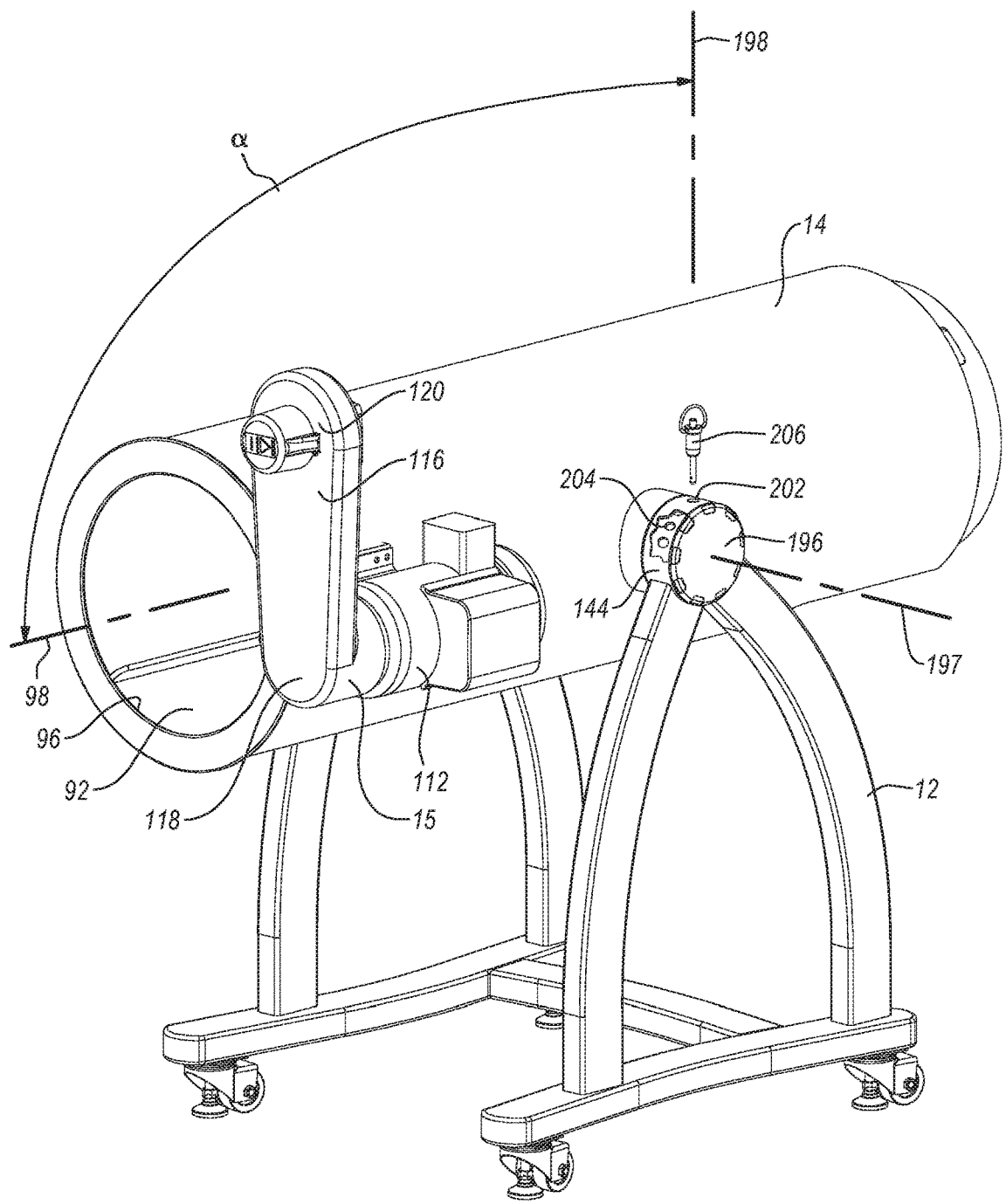
FIG. 6 is a perspective view of the support housing shown in FIG. 1 tilted to a second position.

Returning to FIG. 1, drive motor assembly 15 comprises a drive motor 112 mounted to upper end 84 of support housing 14 by a bracket 114. A support arm 116 has a first end 118 that is pivotably mounted to drive motor 112 and an opposing second end 120. As a result of support arm 116 being pivotably mounted to drive motor 112, support arm 116 can be pivotably moved between a first position and a second position. In the first position, as shown in FIG. 1, support arm 116 projects over access opening 96 of support housing 14 and second end 120 can be aligned with axis 98. In the second position, as shown in FIG. 6, support arm 116 can be pivoted so as to be spaced apart from axis 98 and, more commonly, so that support arm 116 does not extend over or is not aligned with access opening 96. As will be discussed below in greater detail, this pivoting of support arm 116 enables easier access to chamber 92 of support housing 14 for the insertion or removal of container assembly 16. Furthermore, by mounting drive motor 112 on the side of support housing 14, as opposed to above support housing 14, mixing system 10 has a lower height so it can be used in rooms having a lower ceiling.

Figure 5:
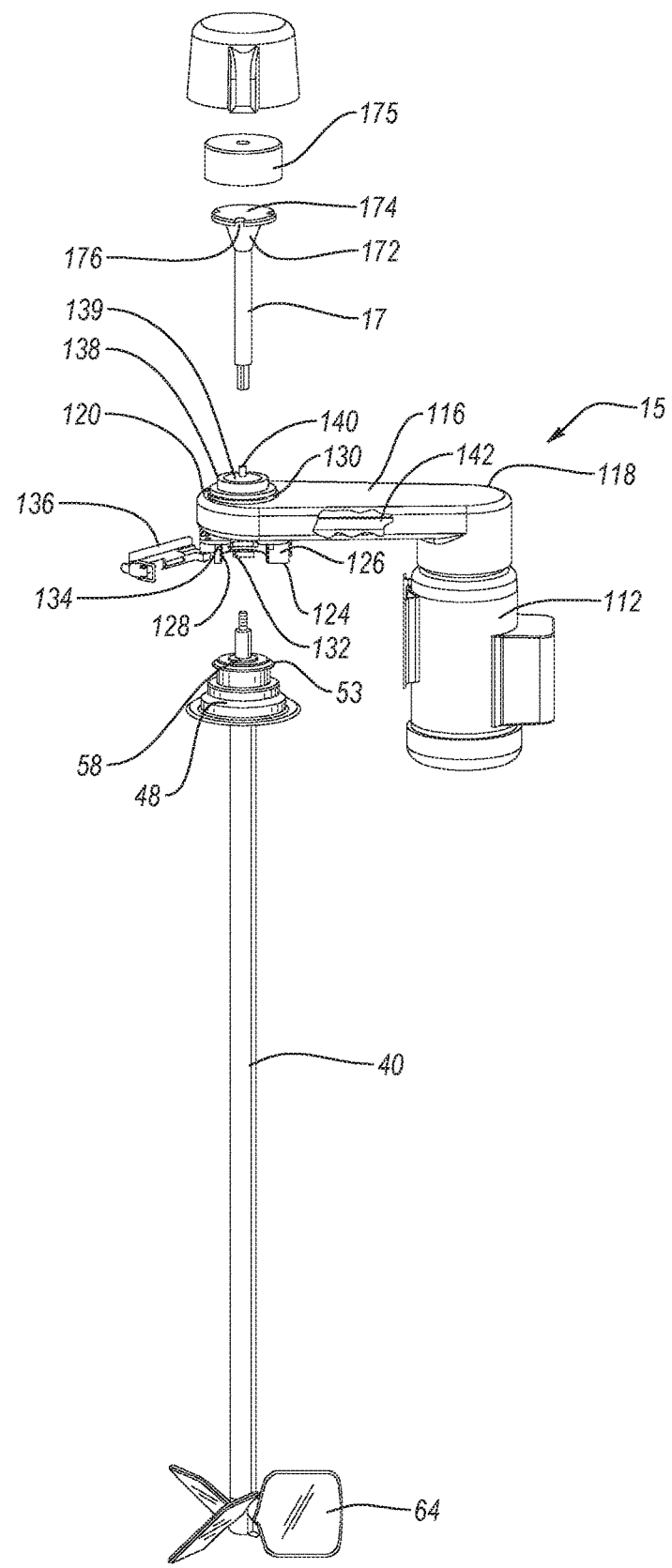
FIG. 5 is a partially exploded view of the impeller assembly, drive shaft, and drive motor assembly of the mixing system shown in FIG. 1.

Turning to FIG. 5, disposed at second end 120 of support arm 116 is a housing 124 having a front face 126. A U-shaped receiving slot 128 is recessed on front face 126. An opening 130 extends down through second end 120 of support arm 116 so as to communicate with receiving slot 128. Receiving slot 128 is bounded by an inside face 132 on which a U-shaped catch slot 134 is recessed. A door 136 is hingedly mounted to housing 124 and selectively closes the opening to receiving slot 128 from front face 126.

A tubular motor mount 138 is rotatably secured within opening 130 on arm 116 so as to align with receiving slot 128. Motor mount 138 bounds a passage 139 extending therethrough. Upstanding from motor mount 138 is a locking pin 140. A drive member 142 extends within arm 116 from drive motor 112 to motor mount 138. Drive motor 112 engages with drive member 142 so that the activation of drive motor 112 facilitates the rotation of motor mount 138 through drive member 142. Drive member 142 can comprise a belt, gear, linkage, drive shaft or any other mechanism that can transfer energy from drive motor 112 to motor mount 138 to facilitate select rotation of motor mount 138 relative to arm 116.

To facilitate attachment of rotational assembly 48 to housing 124, door 136 is rotated to an open position and rotational assembly 48 is horizontally slid into receiving slot 128 from front face 126 of housing 124 so that mounting flange 53 of rotational assembly 48 is received within catch slot 134. Rotational assembly 48 is advanced into receiving slot 128 so that opening 58 of rotational assembly 48 (FIG. 4) aligns with passage 139 extending through motor mount 138. In this position, door 136 is moved to the closed position and secured in place by a latch or other locking mechanism so that rotational assembly 48 is locked to drive motor assembly 15.

Drive shaft 17 is configured to pass through motor mount 138 so that engaging portion 172 of drive shaft 17 is retained within motor mount 138 and locking pin 140 of motor mount 138 is received within notch 176 of drive shaft 17. A cap 175 can then be threaded or otherwise secured onto motor mount 138 so as to secure drive shaft 17 in place. In this configuration, rotation of motor mount 138 by drive motor 112 facilitates rotation of drive shaft 17. Further discussion of drive motor assembly 15 and how it engages with drive shaft 17 and alternative designs of drive motor assembly 15 are discussed in US Patent Publication No. 2011/0188928 which was previously incorporated herein by specific reference.

Returning to FIG. 1, stand 12 comprises a base 186 that can directly rest on a floor surface or can be supported on a floor surface by wheels 188, adjustable legs 190, or the like. Upstanding from base 186 on opposing sides of support housing 14 are braces 192A and 192B. Support housing 14 is pivotably mounted to braces 192A and 192B. Specifically, each brace 192A and 192B has a collar 194 mounted on the end thereof. Axles 196 outwardly project from the opposing sides of sidewall 82 of support housing 14 and are rotatably received within corresponding collars 194. As such, support housing 14 can pivot relative stand 12 by axles 196 rotating within collars 194. An axis 197 extends through axles 196 about which support housing 14 rotates. A bearing can be disposed between each axle 196 and corresponding collars 194 to facilitate ease of rotation.

In the depicted configuration, support housing 14 can be pivoted from a first position to a second position. In the first position, as shown in FIG. 1, longitudinal axis 98 of support housing 14 can be aligned with a vertical axis 198. In the second position, as shown in FIG. 6, support housing 14 can be pivoted so that longitudinal axis 98 is disposed at an angle α relative to vertical axis 198. In one embodiment, support housing 14 can tilt forward and/or backward over an angle α of at least 145° relative to vertical. In other embodiments, support housing 14 can tilt forward and/or backwards over an angle α of at least 130°, 100°, 75°, 45°, or 15° relative to vertical. Other angles can also be used.

The ability to pivot support housing 14 produces a number of unique benefits. For example, by pivoting support housing 14 at approximately 90°, it becomes easy for an operator to access chamber 92 of support housing 14 through access opening 96. The operator can thus easily insert, adjust, or remove container assembly 16 from chamber 92 while standing on the floor. This is particularly helpful where support housing 14 has an extended length that would normally require an operator to access chamber 92 through the use of a ladder or other support structure. Slots 100 and 102 and opening 103 (FIG. 1) are also easily accessed when support housing 14 is tilted to the second position for manipulating container 18 and aligning ports and related tubing. In addition to assisting in the placement of container assembly 16, the tilting of support housing 14 also assists in the placement of drive shaft 17 (FIG. 3). That is, it can be much easier to horizontally insert drive shaft 17 through motor mount 138 while standing on the ground rather than trying to vertically elevate drive shaft 17 above support housing 14 while standing on a ladder or other platform.

In addition, mixing system 10 may be operated in a room with a ceiling that is low relative to the height of support housing 14. In this situation, the ceiling may be so low that it would be impossible to vertically raise drive shaft 17 above support housing 14 for insertion through motor mount 138. As such, the ability to tilt support housing 14 broadens the locations in which mixing system 10 can be used.

Figure 9:
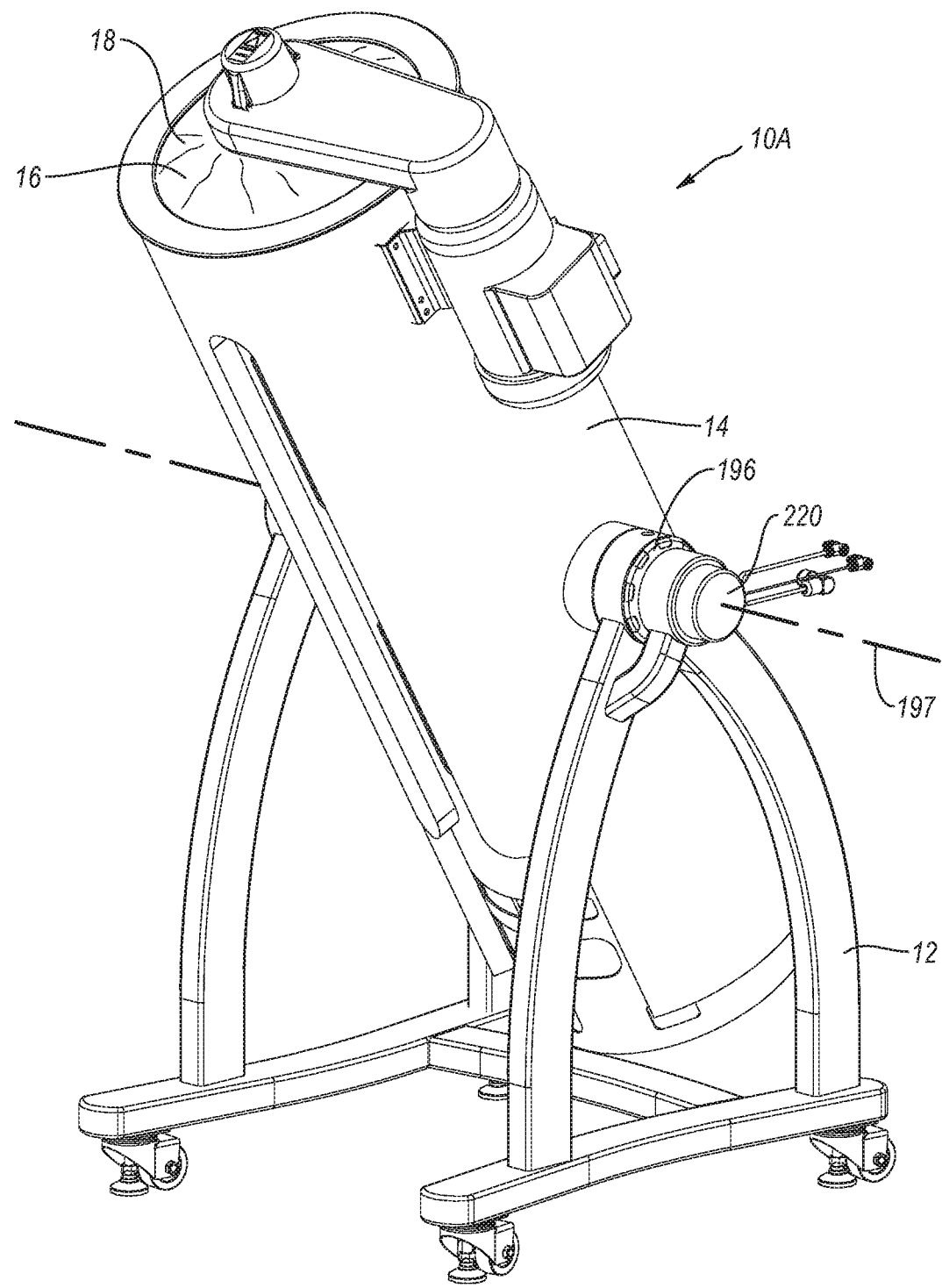
FIG. 9 is a perspective view of the fluid mixing system shown in FIG. 8 with the support housing in a forward tilt position.

Another benefit derived from the ability to tilt support housing 14 is that it assists in the draining of container 18. For example, when fluid is drained out through a drain line extending through the floor of traditional support housing, volumes of fluid can pool on the floor within the flexible container and not flow to the drain line. For example, the fluid can get trapped or blocked by folds of the container. The container must then be manually manipulated to try and get the fluid to flow to the drain line. This can be very difficult with large containers. In present invention, even if the fluid does initially pool on the floor, by tilting support housing 14, such as shown in FIG. 9, the fluid can be forced to flow to drain port 38 and out drain line 39. The flow of fluid through drain line 39 can be controlled by a valve 41 (FIG. 2) coupled therewith. As such, embodiments of the inventive mixing system 10 enable a more complete draining or at least an easier draining of fluid from container 18. When draining through drain line 39, support housing 14 is typically tilted so that longitudinal axis 98 is at an angle relative to vertical that is in a range between about 2° to about 45° with about 5° to about 25° or about 5° to about 15° being more common. Other angles can also be used.

In one embodiment of the present invention, means are provided for releasably locking support housing 14 relative to stand 12. By way of example and not by limitation, as depicted in FIG. 6, an opening 202 extends through collar 194 while a plurality of radially spaced apart openings 204 are formed on axial 196. When opening 202 and one of openings 204 align, a locking pin 206 can be passed into the aligned openings for locking support housing 14 relative to stand 12. By using this configuration, support housing 14 can be locked in the vertical position, as shown in FIG. 1, in a horizontal position, as shown in FIG. 6, or at a variety of other angled orientations. It is appreciated that there are a variety of other locking mechanisms that can be used to lock support housing 14 relative to stand 12. For example, different fasteners, clamps, brakes, blocks, or other stopping mechanisms can be mounted at the junction between axle 196 and collar 194 or can be mounted at a separate location so as to directly secure support housing 14 to prevent the pivoting thereof.

During use, locking pin 206 is removed or the other locking mechanism is released and support housing 14 is rotated to a desired orientation which is typically in a range between about 45° to about 135° relative to vertical. Support arm 116 is then rotated to the second position (FIG. 6) so that access opening 96 to chamber 92 is freely exposed. Container assembly 16 (FIG. 1) is then manually positioned and orientated within chamber 92 of support housing 14 with the port, drain line, and sparge line being fed out through their corresponding opening and slots on support housing 14 as previously discussed.

Next, support arm 116 is rotated back to the first position so as to extend over container assembly 16. Rotational assembly 48 is then securely coupled with housing 124 on support arm 116 (FIG. 5) following which drive shaft 17 (FIG. 3) is advanced through motor mount 138 and into impeller assembly 40 so as to engage with hub 54 and impeller 64.

Once drive shaft 17 is properly positioned, support housing 14 can be rotated back to its vertical or other desired operating position. Container 18 can then be filed with media or other processing fluids and components. Where container 18 is functioning as a bioreactor or fermentor, cells or microorganisms along with nutrients and other standard components can be added to container. Before or after adding the different components, drive motor assembly 15 can be activated causing drive shaft 17 to rotate impeller 64 and thereby mix or suspend the fluid within container 18. Once the fluid processing is complete, the fluid can be drained out through drain line 39. Support housing 14 can be tilted to facilitate draining all of the fluid out of container 18. The reverse of the above process can then be used to remove container assembly 16 from support housing 14.

In one embodiment of the present invention, means are provided for mixing the fluid within container 18 without movement of support housing 14. Impeller assembly 40 in conjunction with drive shaft 17, as discussed above, is one example of such means for mixing. It is appreciated, however, that impeller assembly 40 and drive shaft 17 can have different configurations. For example, two or more impellers can be spaced apart along tubular connector 42. Drive shaft 17 can engage each of the impellers but it is not required.

In another alternative embodiment, it is appreciated that drive shaft 17 need not directly engage each of the hub 54 and impeller 64. For example, drive shaft 17 could engage hub 54 but not impeller 64. In this embodiment, rotation of hub 54 would cause rotation of tubular connector 42 which would then indirectly cause rotation of impeller 64. Likewise, drive shaft 17 need not engage with hub 54. In this example, the rotation of impeller 64 by drive shaft 17 causes the rotation of tubular connector 42 which then indirectly causes rotation of hub 54. The above embodiments can be more commonly used when tubular connector 42 is rigid or substantially rigid but can also be used when tubular connector 42 is flexible.

Figure 7:
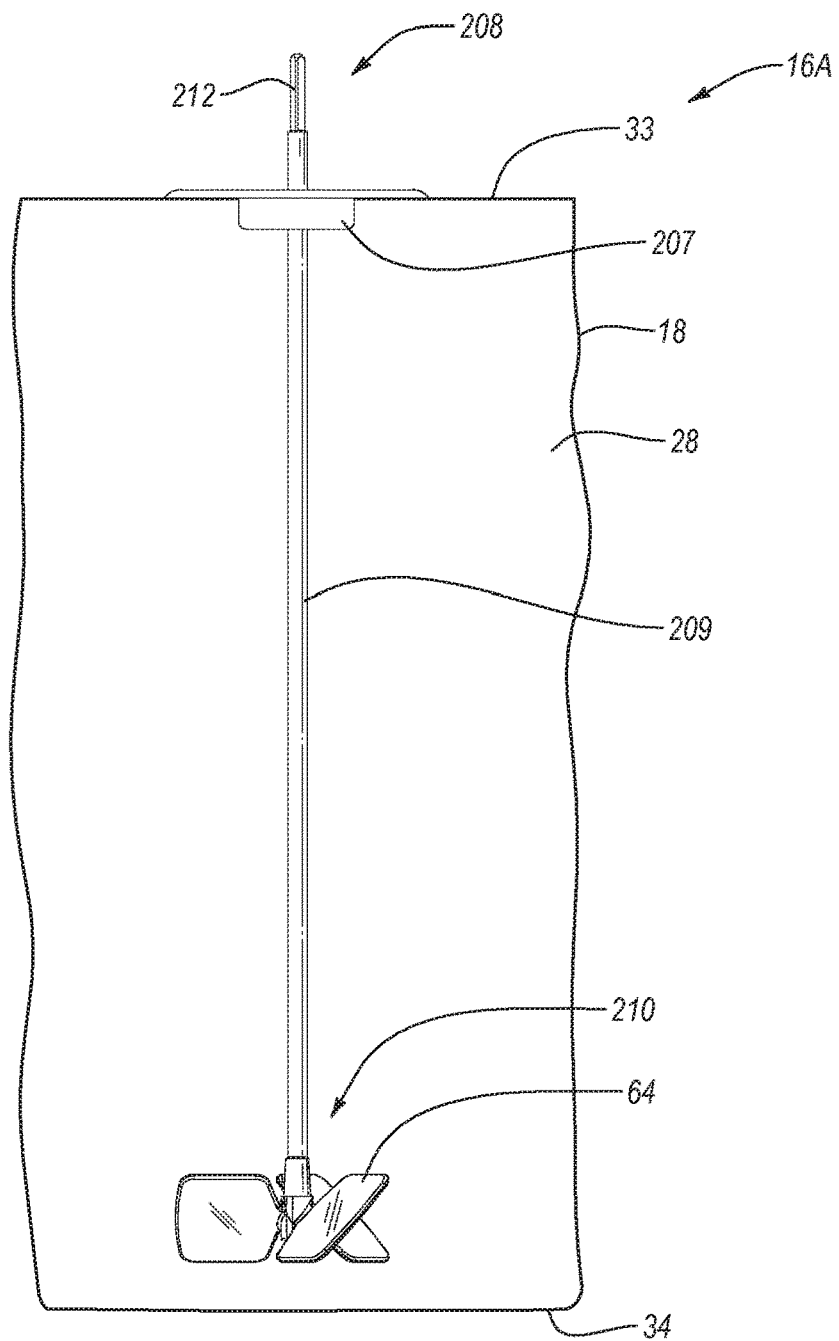
FIG. 7 is a elevated front view of an alternative embodiment of the container assembly shown in FIG. 2.

In another alternative embodiment of the means for mixing, tubular connector 42 can be eliminated. For example, depicted in FIG. 7 is a container assembly 16A that includes container 18. A dynamic seal 207 is mounted on upper end wall 33. A rigid drive shaft 209 passes through dynamic seal 207 and has a first end 208 disposed outside of container 18 and an opposing second end 210 disposed within container 18. Dynamic seal 207 enables drive shaft 209 to freely rotate relative to container 18 while forming an aseptic seal about drive shaft 209. A driver portion 212 or some other engaging surface is formed at first end 208 so that a motor assembly can engage with and rotate drive shaft 209. The motor assembly could be secured to support housing 14 or could be mounted on a separate adjacent structure. Mounted on second end 210 of drive shaft 209 is impeller 64.

In another embodiment of the means for mixing, impeller 64 could be replaced by paddles or other mixing elements that mix by pivoting, swirling, rotating or the like. A mixing element could also be used that is repeatedly raised and lowered within container 18 to facilitate fluid mixing. One example of such a mixing element is disclosed in U.S. Pat. No. 6,908,223 which issued Jun. 21, 2005. Impeller 64 and related drive shaft 17 could also be replaced by a magnetically driven impeller or mixing element disposed within container 18. Where a magnetic mixing element is disposed within container 18, a magnetic driver could be secured to support housing 14, such as on the bottom surface of floor 88 (FIG. 1). The external magnet driver would facilitate rotation or other movement of the magnetic mixing element within container 18. As used herein, the term "mixing element" is broadly intended to cover impellers, paddles, magnetic stir bars, vertical mixers, other mixing bars and the like that can mix fluid within container 18 without the movement of support housing 14.

Figure 8:
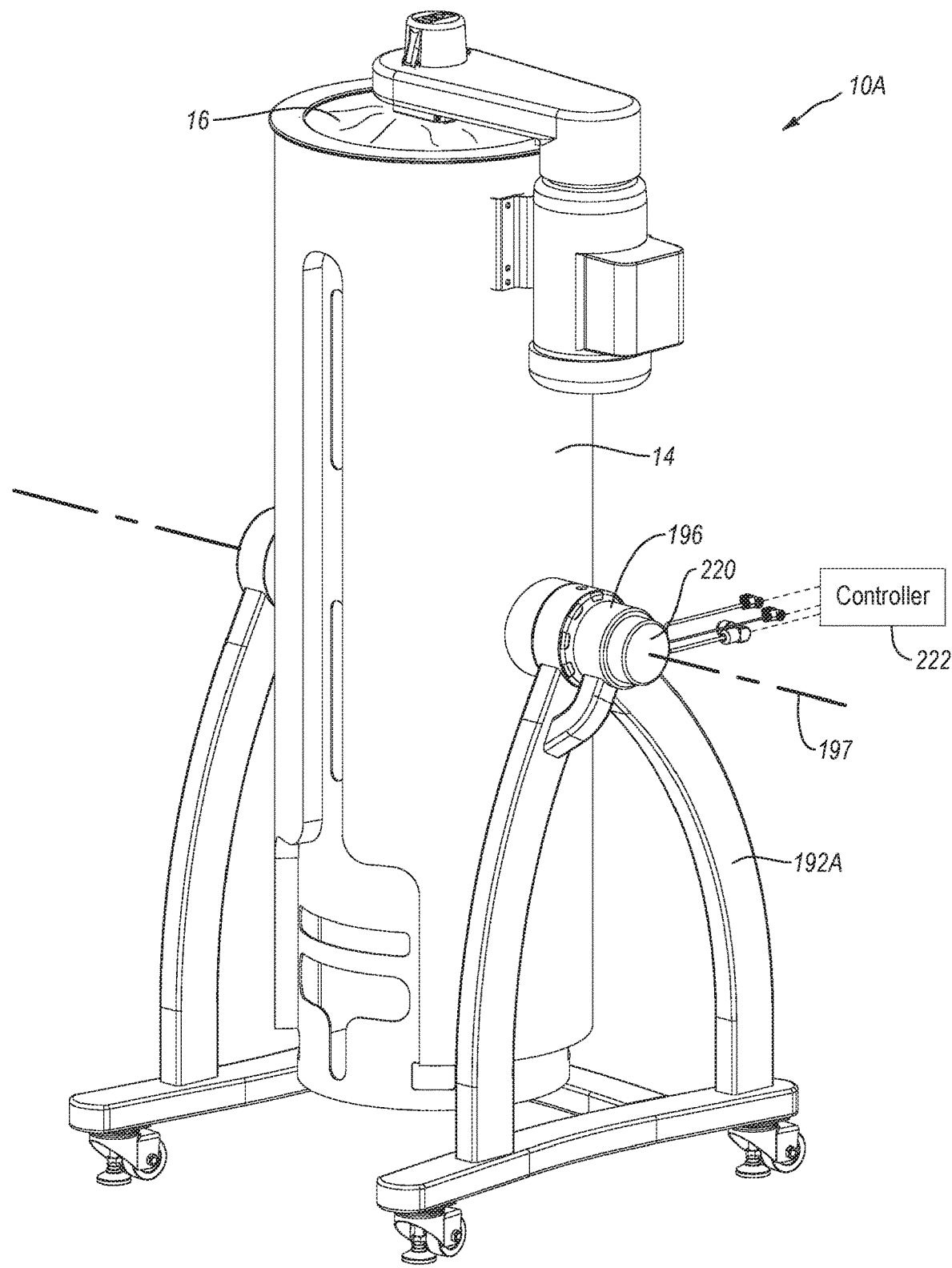
FIG. 8 is an alternative embodiment of a fluid mixing system having a motor and a corresponding controller for rocking of the support housing.
Figure 10:
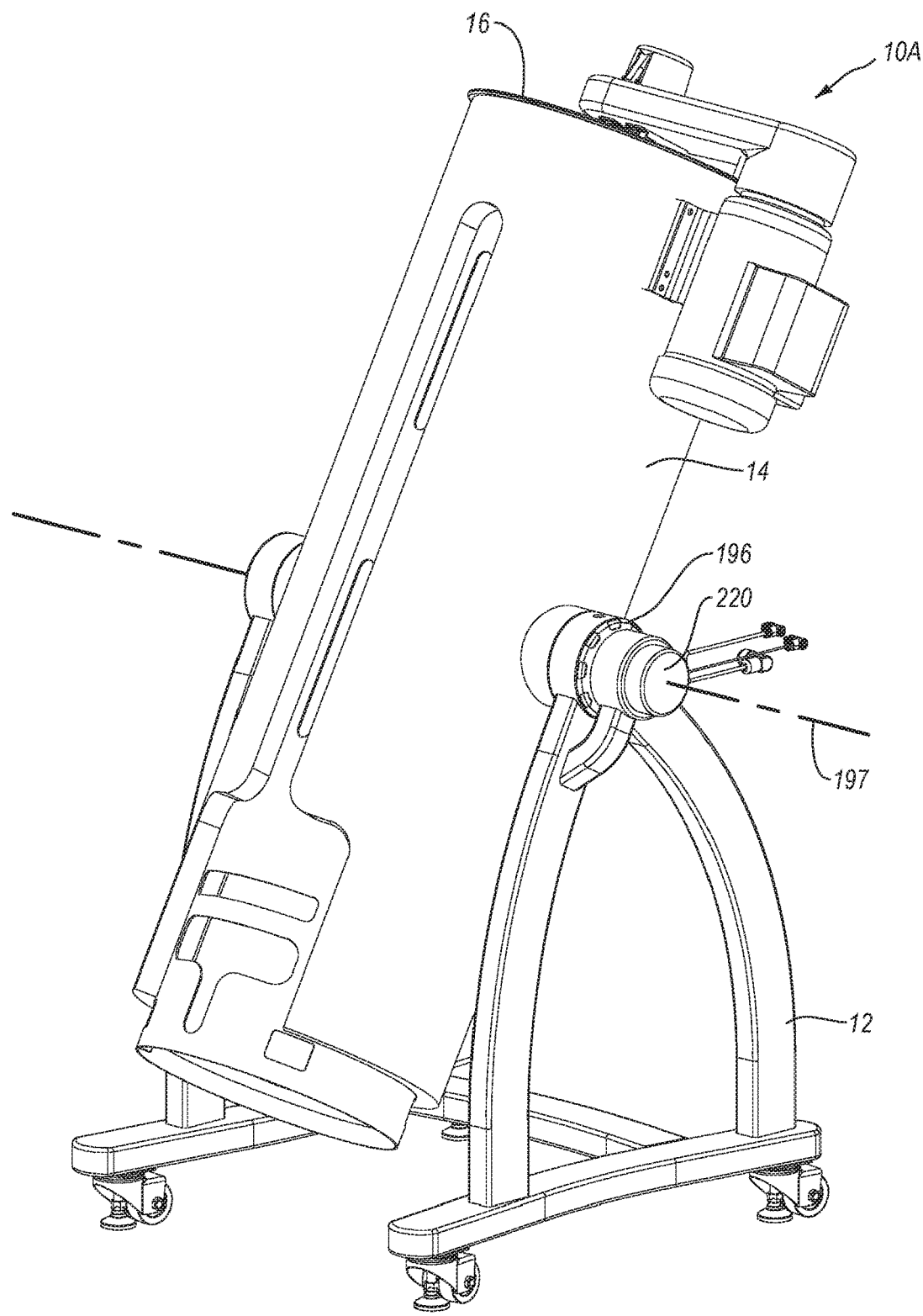
FIG. 10 is a perspective view of the fluid mixing system shown in FIG. 8 with the support housing in a rearward tilt position.

The present invention also includes means for mixing fluid contained within container 18 by repeatedly moving support housing 14 and container 18 contained therein. For example, depicted in FIG. 8 is one embodiment of a fluid mixing system 10A. Like elements between fluid mixing system 10 and 10A are identified by like reference characters. Likewise, all prior discussions and alternatives previously discussed with fluid mixing system 10 are also applicable to fluid mixing system 10A. Fluid mixing system 10A is substantially identical to fluid mixing system 10 except that a motor 220 is mounted on brace 192A and engages with axle 196. Motor 220 is electrically coupled with a controller 222. Controller 222 operates motor 220 so that motor 220 continuously pivots support housing 14 about axis 197 between a forward tilt position as shown in FIG. 9 and a rearward tilt position as shown in FIG. 10. This repeated tilting or rocking of support housing 14 causes fluid within container 18 to mix. In other embodiments, impeller 64 and the other related mixing components can be eliminated and mixing within container 18 can be accomplished only by rocking or otherwise moving support housing 14.

The tilting or rocking of support housing 14 can be accomplished by activating motor 220 until support housing 14 pivots over a certain angle and then deactivating motor 220 so that support housing 14 swings back under gravitational force. Alternatively, motor 220 can be operated to rotate axle 196 is a first direction and then rotate axle 196 in an opposing second direction. In yet other embodiments, a mechanical linkage can be used to produce the discussed rocking while allowing continual motor motion in a single direction. In the depicted embodiment, drive motor assembly 15, drive shaft 17, and impeller assembly 40 can be eliminated. Alternatively, impeller assembly 40 and the related components can be used in conjunction with motor 220. For example, motor 220 can be used to mix small volumes of fluid within container assembly 16 by rocking support housing 13 while impeller assembly 40 or other mixing elements can be used to mix larger volumes of fluid within container assembly 16 without required movement of support housing 13. The different types of mixing systems can also be used concurrently. As such, the type of mixing used can change as the volume of fluid increases within container assembly 16.

When mixing fluid by rocking, the tilting of support housing 14 is typically made over an angle tilted forward and back from vertical that is typically at least 5°, 10° or 15° from vertical. For example, support housing 14 can tilt 10° forward and 10° backward. The angle of tilt during mixing is commonly in a range between about 5° to about 45° from vertical with about 10° to about 30° from vertical being more common. Other angles can also be used. It is appreciated that there are a number of different mechanisms that can be used for continuously rocking support housing 14. For example, rather than using a motor that couples with axle 196, an arm, pulley system, gear assembly, or a variety of other mechanisms can be mounted to the upper or lower end of support housing 14 for mechanically tilting support housing 14 back and forth about axis 197. The above examples of mechanisms for rocking support housing 14 are all examples of means for repeatedly rocking support housing 14 between the forward tilt position and the rearward tilt position.

Figure 11:
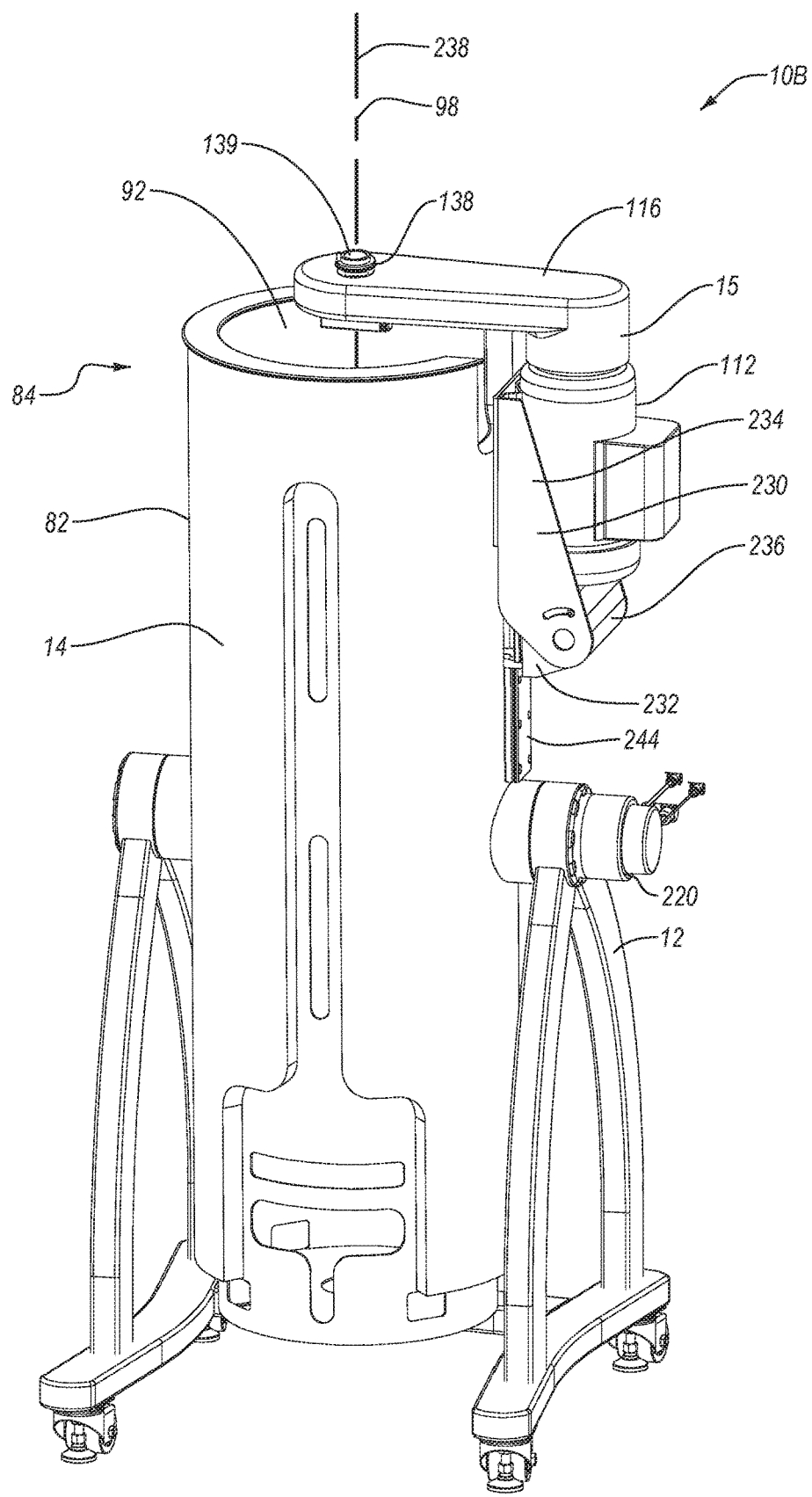
FIG. 11 is a perspective view of an alternative embodiment of a fluid mixing system having a rack for adjustably tilting and elevating the drive motor assembly.

Depicted in FIG. 11 is a perspective view of a fluid mixing system 10B. Like elements between fluid mixing systems 10, 10A and 10B are identified by like reference characters. Likewise, all prior discussion and alternatives previously discussed with fluid mixing systems 10 and 10A are also applicable to fluid mixing system 10B. Fluid mixing system 10B is substantially identical to fluid mixing system 10A except that fluid mixing system 10B includes an adjustable mounting rack 230 that secures drive motor assembly 15 to support housing 14. Mounting rack 230 permit the selective adjustment of the angle at which drive shaft 17 and impeller 64 mounted on the end thereof project into container 18. Specifically, mounting rack 230 comprises a base 232 mounted to sidewall 82 of support housing 14 at or towards upper end 84. An arm 234 is pivotally mounted to base 232 by a hinge 236. Drive motor 112 is mounted on arm 234 so that drive motor assembly 15 rotates concurrently with arm 234 about hinge 236.

Figure 12:
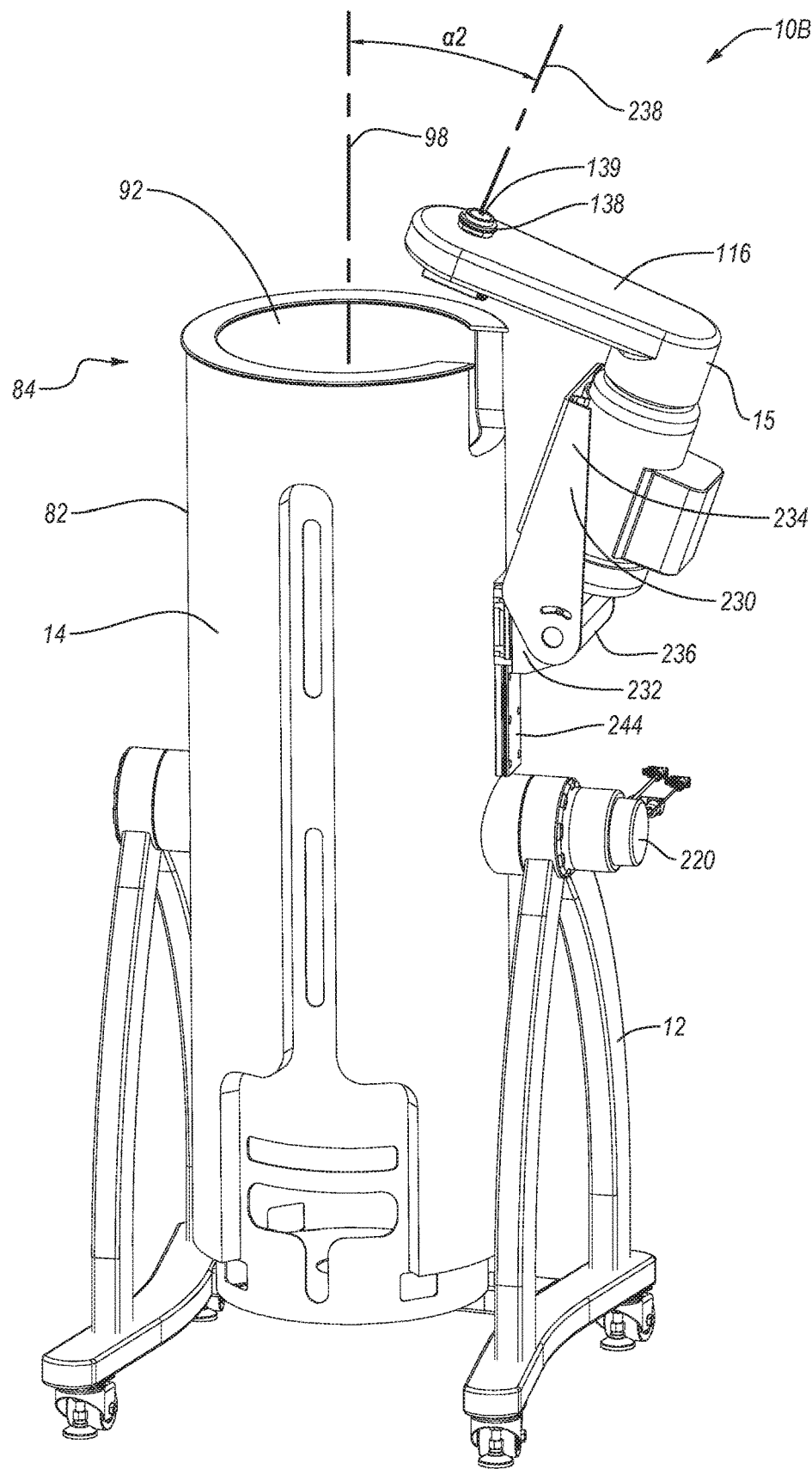
FIG. 12 is a perspective view of the fluid mixing system shown in FIG. 11 with the drive motor assembly tilted to a second position.

Arm 234 can be selectively pivoted about hinge 236 so that a central longitudinal axis 238 that extends through passage 139 of motor mount 138 (axis 238 also extending along the length of drive shaft 17 when drive shaft 17 is received within motor mount 138) can be moved from a first position as shown in FIG. 11 to a second position as shown in FIG. 12. In the first position, axis 238 is aligned with longitudinal axis 98 of chamber 92 of support housing 14. As such, drive shaft 17 and impeller 64 are centrally disposed within container 18 during operation and are vertically disposed when support housing 14 is vertically orientated. Mixing system 10 shown in FIG. 1 produces the same orientation for drive shaft 17 and impeller 64.

In the second position shown in FIG. 12, drive motor assembly 15 is tilted concurrently with arm 234 so that axis 238 is tilted relative to axis 98 at an angle $\alpha_2$. Drive shaft 17 and impeller 64 (FIG. 5) are thus also disposed at angle $\alpha_2$ when within container 18. The angle $\alpha_2$ is typically in a range between about 10° to about 30° or about 5° to about 20° which angle can also be relative to vertical. Other angles can also be used. It can be desirable to adjust the angle of orientation of impeller 64 to achieve optimal mixing for different impellers at different speeds. For example, at slower speeds it can be desirable to tilt impeller 64 to improve mixing, such as by increasing turbulent flow. In view of the foregoing, it is appreciated that support arm 116 can selectively rotate about an axis that is substantially parallel to longitudinal axis 98 (FIG. 6) and can also selectively rotate about an axis that is substantially perpendicular to longitudinal axis 98 (FIG. 12).

With reference to FIG. 11, base 232 of mounting rack 230 is movably mounted to a rail 244 secured to sidewall 82 of support housing 14. Rail 244 typically extends along sidewall 82 parallel to longitudinal axis 98 so that when support housing 14 is vertically orientated, mounting rack 230 can be selectively moved vertically up and down along support housing 14 and then locked at a desired location. The movement of mounting rack 230 also correspondingly moves drive motor assembly 15, which is coupled to mounting rack 230, which can in turn correspondingly move drive shaft 17 and impeller assembly 40 when they are coupled to drive motor assembly 15. The movement of mounting rack 230 can thus adjust the vertical position of impeller 64 within container 18 or can adjust the spacing between floor 88 of support housing 14 and impeller 64. The vertical positioning of impeller 64 can be used to achieve optimal mixing of different levels of fluid within container 18.

Figure 13:
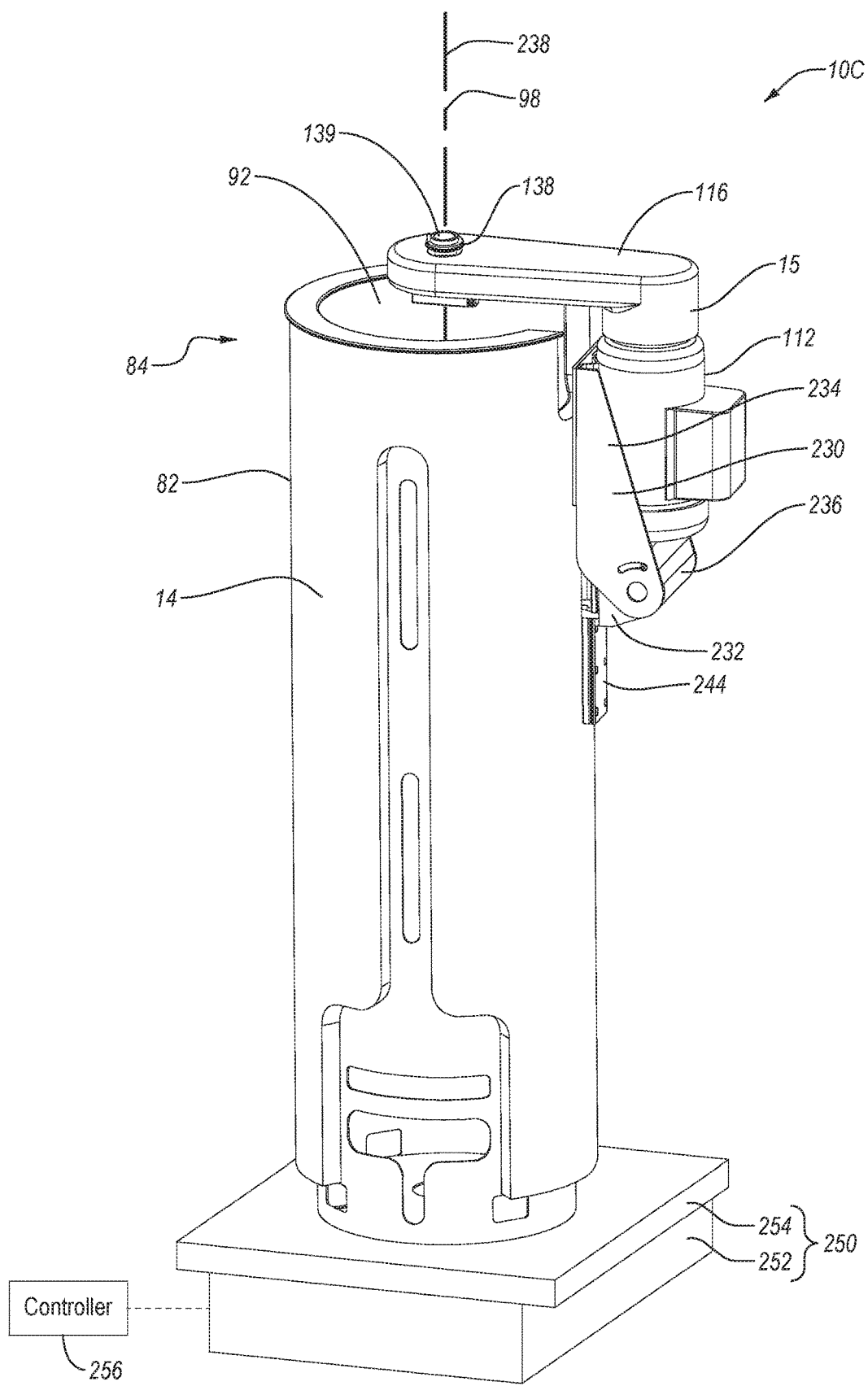
FIG. 13 is a perspective view of an alternative embodiment of a fluid mixing system wherein the support housing is resting on a shaker table.

Depicted in FIG. 13 is a perspective view of a fluid mixing system 10C. Like elements between fluid mixing systems 10, 10A and 10B are identified by like reference characters. Likewise, all prior discussions and alternatives previously discussed with regard to fluid mixing systems 10, 10A and 10B are also applicable to like elements of fluid mixing system 10C. Fluid mixing system 10C is substantially identical to fluid mixing system 10B except that support stand 12 and motor 220 have been removed and support housing 14 now rests on a shaker table 250. Shaker table 250 comprises a base 252 and a platform 254 supported on base 252. Base 252 includes a drive mechanism that reciprocally moves platform 254 in one or two dimensions in a horizontal plane. A controller 256 can be used to activate shaker table 250 and control the rate of reciprocal movement of platform 254. It is appreciated that shaker tables are known in the art and that any off the shelf or custom shaker table configured to handle the load capacity of support housing 14, container assembly 16 and the related fluid can be used.

Support housing 14 rests on platform 254 of shaker table 250 so that fluid within container assembly 16 can be selectively mixed when shaker table 250 is activated. As previously discussed with regard to using motor 220 to rock support housing 14, it is appreciated that shaker table 250 would more commonly be used for mixing low volumes of fluid within container assembly 16 and that impeller 64 or other mixing elements would be used for mixing the fluid within container assembly 16 for larger volumes of fluid. In still other embodiments other mechanisms can be used for mixing fluid within container assembly 16 by movement of support housing 14. For example, support housing 14 can be mounted on a table that reciprocally or continuously tilts, pivots, swivels or the like so as to produce mixing of the fluid within container assembly 16.

It is appreciated that mixing systems 10A-10C, which each have two different types of mixing mechanisms, can achieve a number of unique benefits, especially when they are being used as a bioreactor or fermentor. For example, as previously mentioned, when growing biological cultures it is desirable that the culture be continuously and homogeneously mixed so as to achieve proper feeding and mass transfer of gases within the culture. Proper mixing can be achieved for low volumes of culture or fluids within container assembly 16 by simply moving support housing 14, such as in a reciprocal of continuous fashion. As previously discussed, the movement of support housing 14 needed for mixing can be accomplished in a variety of different manners such as rocking, shaking, swiveling, tilting or otherwise moving support housing 14. What constitutes a "low" volume of fluid is dependent in part on the size and shape of container assembly 16. The concept is that for relatively large container assemblies 16 containing only a very low volume of fluid, impeller 64 or other mixing elements may not properly function for mixing the fluid. For example, impeller 64 may not reach the fluid for mixing or, if the impeller does reach the fluid, the impeller may be so large relative to the volume of fluid that operation of impeller 64 would create splashing or apply other unwanted shear forces on the culture which would be detrimental to the culture. The same can also be true for the other types of mixing elements. In contrast, mixing by rocking, shaking, tilting or the like of support housing 14/container assembly 16 can achieve the desired mixing without applying unwanted shear forces.

As the culture grows, additional media and other components are added, thereby increasing the volume of the fluid. The media can be added in a slow continuous fashion or at staged intervals. Mixing by movement of support housing 14/container assembly 16 can be used until the volume of fluid within container assembly 16 gets so large that that form of mixing can no longer achieve the desired mixing rate. At that stage, movement of support housing 14/container assembly 16 for mixing can be stopped and mixing by impeller 64 or other mixing element within container assembly 16 can be activated. In some embodiments, it may be desirable to have a gradual transition between the two different mixing techniques. For example, mixing by impeller 64 may be gradually started at low speeds while mixing by movement of support housing 14/container assembly 16 is maintained. As the culture volume further increases, the speed of rotation of impeller 64 can be gradually increased while the mixing by movement of support housing 14/container assembly 16 is gradually decreased until eventually stopped. As the volume of culture continues to increase within container assembly 16, it may be necessary to adjust the vertical height, orientation and/or speed of impeller 64 within container assembly 16 to maintain the desired mixing for the corresponding volume. This adjustment can be achieved as previously discussed.

Once the culture has reached a desired batch size, the culture may be gradually removed from container assembly 16 as needed. As the culture is removed and the volume decreases, the mixing conditions can be reversed. That is, as the volume decreases, the mixing by impeller 64 or other mixing element within container assembly 16 can be slowed or stopped while mixing by moving support housing 14/container assembly 16 is increased.

In view of the foregoing, embodiments of the present invention produce desired mixing of the culture over a wide range of volumes while eliminating the risk of unwanted shear forces. Furthermore, the culture can be grown over a wide range of volumes within a single container. This eliminates or reduces the number of different containers that the culture needs to be transferred into during both the growth stage and the removal stage. By reducing the number of transfers between containers, there is less down time in processing, less risk of contamination, less material waste, and fewer man hours required. As a result, the culture product is produced safer and with lower production costs.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for mixing a fluid comprising:
dispensing a first volume of a fluid into a flexible container, the flexible container being at least partially disposed within a chamber of a support housing;
repeatedly moving the support housing and the flexible container contained therein so as to mix the first volume of fluid within the flexible container;
adding further fluid into the flexible container after moving the support housing to form a second volume of fluid; and
manipulating a mixing element within the flexible container so as to mix the second volume of fluid.

2. The method as recited in claim 1, wherein repeatedly moving the support housing comprises repeatedly rocking, shaking, tilting, or swiveling the support housing.

3. The method as recited in claim 1, wherein manipulating the mixing element comprises rotating an impeller or magnetic stir bar within the flexible container.

4. The method as recited in claim 1, wherein manipulating the mixing element comprises pivoting, swiveling, or vertically raising and lowering the mixing element within the flexible container.

5. The method as recited in claim 1, wherein the step of repeatedly moving the support housing occurs without manipulating the mixing element within the flexible container.

6. The method as recited in claim 1, wherein the step of manipulating the mixing element further comprises concurrently, repeatedly moving the support housing and the flexible container contained therein.

7. The method as recited in claim 1, wherein the step of manipulating the mixing element occurs without repeatedly moving the support housing and the flexible container contained therein.

8. The method as recited in claim 1, wherein the first volume of fluid comprises cells or microorganisms and the further fluid is added based on the growth of the cells or microorganisms within the flexible container.

9. The method as recited in claim 1, further comprising sparging a gas into the first volume of the fluid.

10. The method as recited in claim 1, wherein the flexible container comprises a flexible bag that is comprised of one or more sheets of a polymeric film.

11. The method as recited in claim 1, wherein the mixing element comprises an impeller and the method further comprises adjusting a location of the impeller within the flexible container based on the volume of fluid within the flexible container.

12. A method for mixing a fluid comprising:
   tilting a support housing that comprises a sidewall that encircles a chamber, an access opening formed at a first end of the sidewall, and a floor disposed at a second end of the sidewall, an axis extending through the chamber so as to pass through the floor and the access opening, the support housing being tilted from a first position wherein the axis is vertically oriented to a second position wherein the axis is at least 45° from vertical;
   inserting a container assembly into the chamber of the support housing when the support housing is in the second position, the container assembly comprising a flexible bag bounding a compartment adapted to hold a fluid;
   moving the support housing containing the container assembly back to the first position;
   delivering a fluid into the compartment of the flexible bag; and
   mixing the fluid within the compartment of the flexible bag.

13. The method as recited in claim 12, wherein the step of mixing the fluid comprises manipulating a mixing element located within the compartment of the flexible bag.

14. The method as recited in claim 13, further comprising:
   after the step of tilting the support housing, moving an arm from a first position wherein the arm projects over the access opening so that the axis passes through the arm to a second position wherein the arm is spaced apart from the axis; and
   moving the arm from the second position back to the first position after inserting the container assembly into the chamber of the support housing.

15. The method as recited in claim 14, further comprising:
   coupling a drive shaft to the arm and to the mixing element; and
   rotating the drive shaft.

16. The method as recited in claim 12, wherein the step of mixing the fluid comprises repeatedly moving the support housing and the flexible container contained therein.

17. The method as recited in claim 16, wherein the step of repeatedly moving the support housing comprises activating a motor so as to cause the support housing to repeatedly rock between a forward tilt position and an opposing rearward tilt position.

18. The method as recited in claim 12, wherein the step of tilting the support housing comprises tilting the support housing so that the axis is at least 75° from vertical when in the second position.

\* \* \* \* \*